US010475992B2

(12) United States Patent
Le Neel et al.

(10) Patent No.: US 10,475,992 B2
(45) Date of Patent: Nov. 12, 2019

(54) DURABLE MINIATURE GAS COMPOSITION DETECTOR HAVING FAST RESPONSE TIME

(71) Applicant: STMicroelectronics Pte Ltd, Singapore (SG)

(72) Inventors: Olivier Le Neel, Singapore (SG); Ravi Shankar, Singapore (SG)

(73) Assignee: STMicroelectronics Pte Ltd, Singapore (SG)

( * ) Notice: Subject to any disclaimer, the term of this patent is extended or adjusted under 35 U.S.C. 154(b) by 0 days.

(21) Appl. No.: 15/783,293

(22) Filed: Oct. 13, 2017

(65) Prior Publication Data

US 2018/0090678 A1   Mar. 29, 2018

Related U.S. Application Data

(60) Continuation of application No. 14/982,600, filed on Dec. 29, 2015, now Pat. No. 9,818,937, which is a
(Continued)

(51) Int. Cl.
*H01L 43/14* (2006.01)
*G01N 27/74* (2006.01)
(Continued)

(52) U.S. Cl.
CPC .............. *H01L 43/14* (2013.01); *G01N 27/74* (2013.01); *H01L 21/8234* (2013.01);
(Continued)

(58) Field of Classification Search
None
See application file for complete search history.

(56) References Cited

U.S. PATENT DOCUMENTS 4,667,157 A   5/1987   Ciammaichella et al.
4,772,848 A   9/1988   Hummel
(Continued)

OTHER PUBLICATIONS

Konig et al. 'A Novel Micro Paramagnetic Oxygen Sensor Based on an Anisotropic Magneto Resistance-Device', IEEE Sensors 2010 Conference, pp. 1496-1499 (Year: 2010).*
(Continued)

*Primary Examiner* — Shaun M Campbell
(74) *Attorney, Agent, or Firm* — Seed IP Law Group LLP

(57) ABSTRACT

A miniature oxygen sensor makes use of paramagnetic properties of oxygen gas to provide a fast response time, low power consumption, improved accuracy and sensitivity, and superior durability. The miniature oxygen sensor disclosed maintains a sample of ambient air within a micro-channel formed in a semiconductor substrate. $O_2$ molecules segregate in response to an applied magnetic field, thereby establishing a measureable Hall voltage. Oxygen present in the sample of ambient air can be deduced from a change in Hall voltage with variation in the applied magnetic field. The magnetic field can be applied either by an external magnet or by a thin film magnet integrated into a gas sensing cavity within the micro-channel. A differential sensor further includes a reference element containing an unmagnetized control sample. The miniature oxygen sensor is suitable for use as a real-time air quality monitor in consumer products such as smart phones.

16 Claims, 12 Drawing Sheets

Related U.S. Application Data division of application No. 13/853,805, filed on Mar. 29, 2013, now Pat. No. 9,234,876.

(51) Int. Cl.
*H01L 21/8234* (2006.01)
*H01L 43/04* (2006.01)
*H01L 43/06* (2006.01)
*H01L 43/10* (2006.01)

(52) U.S. Cl.
CPC ............ *H01L 43/04* (2013.01); *H01L 43/065* (2013.01); *H01L 43/10* (2013.01); *Y10T 29/4913* (2015.01)

(56) References Cited

U.S. PATENT DOCUMENTS

| | | | |
|---|---|---|---|
| 4,848,148 A | 7/1989 | Capriotti et al. | |
| 6,430,987 B1 | 8/2002 | Stark | |
| 6,596,236 B2 | 7/2003 | DiMeo, Jr. et al. | |
| 7,247,246 B2 | 7/2007 | Nasiri et al. | |
| 7,250,112 B2 | 7/2007 | Nasiri et al. | |
| 7,621,183 B2 | 11/2009 | Seeger et al. | |
| 7,767,484 B2 | 8/2010 | Ayazi | |
| 8,124,953 B2* | 2/2012 | Elian .................. | G01L 19/141 257/114 |
| 8,542,009 B2 | 9/2013 | Duric et al. | |
| 9,234,876 B2* | 1/2016 | Le Neel ............... | G01N 27/74 |
| 2001/0045121 A1* | 11/2001 | Chiba .................. | G01N 27/74 73/25.02 |
| 2005/0079647 A1 | 4/2005 | Abraham et al. | |
| 2007/0113642 A1 | 5/2007 | Bonne et al. | |
| 2008/0184799 A1 | 8/2008 | Phan Le et al. | |
| 2010/0264917 A1 | 10/2010 | Budker et al. | |
| 2011/0018532 A1* | 1/2011 | Florescu ............ | G01N 33/54326 324/251 |
| 2011/0057651 A1* | 3/2011 | Duric .................. | G01N 27/74 324/252 |
| 2011/0094293 A1* | 4/2011 | Klein .................. | G01N 27/74 73/31.05 |
| 2011/0199102 A1 | 8/2011 | Garcia et al. | |
| 2011/0252868 A1 | 10/2011 | Döring et al. | |
| 2014/0366640 A1* | 12/2014 | Sidhwa ............... | G01F 1/56 73/861.12 |
| 2017/0082581 A1 | 3/2017 | Breuer et al. | |

OTHER PUBLICATIONS

"Paramagnetic Cells", *Systech Instruments*, May 4 v. 1.03.
"The Hall Effect" Wikipedia web page, retrieved extract from Wikipedia at http://en.wikipedia.org/wiki/Hall_efffect.
Delgado, Raül D., Tin Oxide Gas Sensors: An Electrochemical Approach, (2002) *Ph.D. Thesis*, University de Barcelona.
Diebold, Ulrike, "The Surface Science of Titanium Dioxide", Department of Physics, Tulane University, New Orleans LA (2002), as published in *Surface science reports*, vol. 48, pp. 53-229 (2003).
Milano, Shaun, "Allegro Hall-Effect Sensor ICs," *Product Information*, © 2009-2013, Allegro MicroSystems, LLC, retrieved from http://www.allegromicro.com.
Seeger et al., "Development of High-Performance, High-Volume Consumer MEMS Gyroscopes," InvenSense, 2010, 5 pages.
Satter, Edgar A. S., "Development of Thick Film Gas Sensor for Oxygen Detection at Trace Levels" *PhD Thesis*, (2006), Department of Electronic Engineering, Universitat Rovira I Virgili.

\* cited by examiner

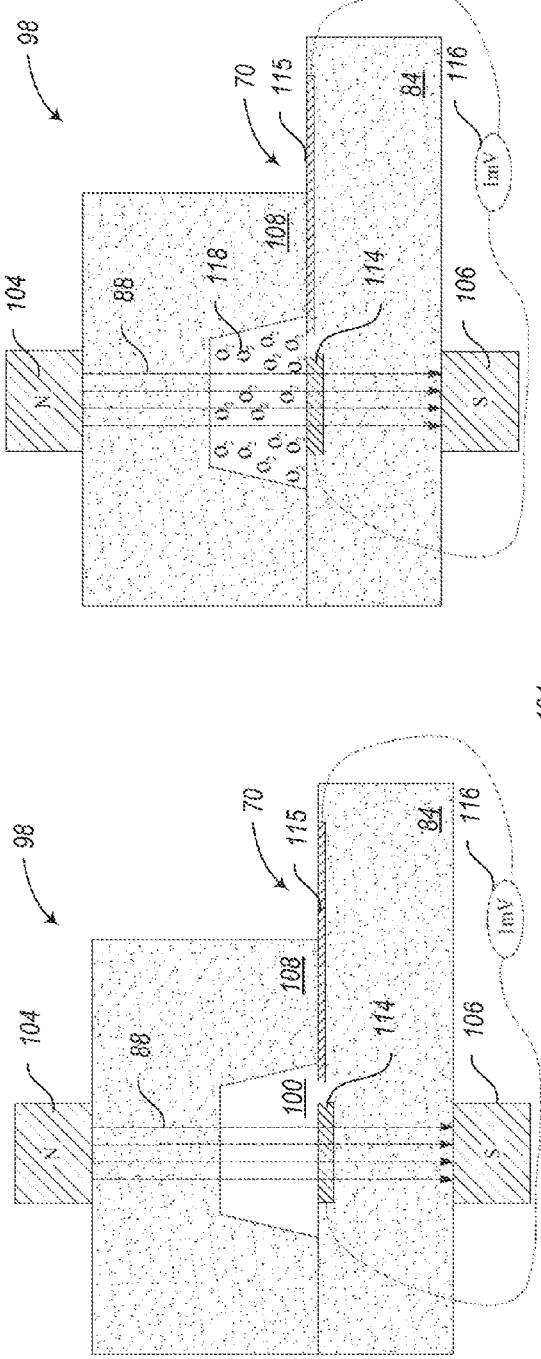
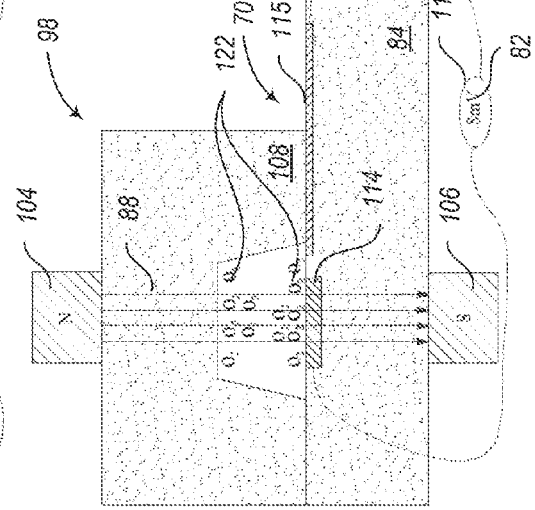
Fig. 6A
Fig. 6B
Fig. 6C

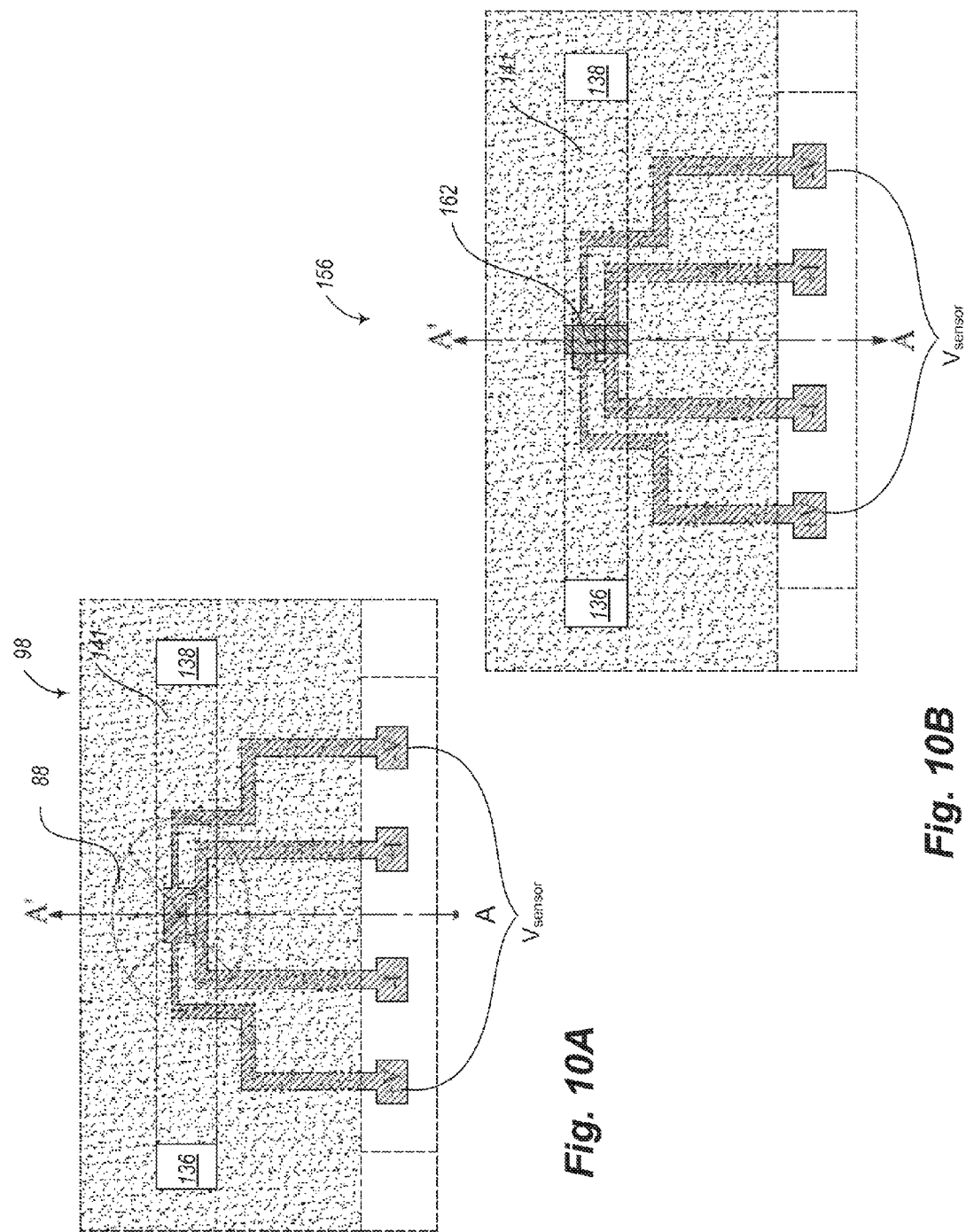

DURABLE MINIATURE GAS COMPOSITION DETECTOR HAVING FAST RESPONSE TIME

CROSS REFERENCE TO RELATED APPLICATIONS

The present application is a continuation of U.S. patent application Ser. No. 14/982,600, filed Dec. 29, 2015, which is a divisional of U.S. patent application Ser. No. 13/853,805, filed Mar. 29, 2013, issued as U.S. Pat. No. 9,234,876, which are incorporated herein by reference in their entirety.

BACKGROUND

Technical Field

The present disclosure relates to the fabrication of microelectronic environmental sensors, such as gas composition sensors.

Description of the Related Art

Oxygen is one of the most important and abundant chemical species. It constitutes 21% of the earth's atmosphere, and is needed to sustain plant and animal life. Oxygen is also widely employed for industrial purposes. Conventional oxygen sensors are widely used in laboratory and industrial applications, wherever oxygen is consumed, emitted, or otherwise present. Such oxygen sensors, for example, those shown in FIGS. 2 and 3 below, generally have large scale form factors, tend to be expensive, and typically require involvement of skilled operators.

With the advent of micro-mechanical systems, deployment of sensors and feedback control systems in smaller scale applications is made possible. For instance, many electronic devices now contain environmental sensors. In one example, electronic thermostats connected to climate control systems rely on temperature sensors to trigger activation of furnaces and air conditioners. In another example, electronic weather stations rely on internal temperature sensors, barometric pressure sensors, and humidity sensors. Small scale consumer products such as motion activated air fresheners can make use of sensors that detect changes in ambient light, or changes in air flow.

Miniature sensors that are typically embedded on board mobile computing devices such as smart phones include, for example, magnetic field sensors used to determine orientation of the smart phone relative to the earth's magnetic field. Providing additional environmental sensors within smart phones, tablet computers, and the like may encourage program developers to create applications that otherwise might not be possible. In particular, if miniaturized gas sensors could be provided in consumer products, they might find wide use for medical applications such as pulmonary monitoring.

BRIEF SUMMARY

A miniature gas sensor leverages paramagnetic properties of oxygen gas to measure a Hall voltage induced by gas molecule segregation in an applied magnetic field. Certain atoms, including oxygen, have a net magnetic dipole moment that tends to align in an external magnetic field. While such paramagnetic effects can be canceled out by collisions on a macroscopic scale, they can be sustained more easily across small distances that exist within microelectronic devices.

The miniature sensor described can be implemented to detect gases other than oxygen, provided the subject gas also exhibits paramagnetism or another property that can be similarly manipulated.

The miniature oxygen sensor disclosed maintains a sample of ambient air within a micro-channel formed in a semiconductor substrate. The micro-channel contains a constant volume of $O_2$ gas. When subjected to a magnetic field, the $O_2$ molecules align with the magnetic field and segregate, thereby establishing a measureable Hall voltage. A concentration of oxygen present in the sample of ambient air can be deduced from a change in Hall voltage in response to at least a momentary variation in the applied magnetic field. The magnetic field can be applied either by an external magnet or by a thin film magnet that is integrated into the micro-channel.

A differential sensor further includes a second microchannel containing a control sample to which a magnetic field is not applied. Comparison of the Hall voltage measurement and a control measurement yields a differential Hall voltage measurement having improved accuracy.

BRIEF DESCRIPTION OF THE SEVERAL VIEWS OF THE DRAWINGS

In the drawings, identical reference numbers identify similar elements. The sizes and relative positions of elements in the drawings are not necessarily drawn to scale.

FIGS. 6A-6C are cross sections along a cut line A-A' (shown in FIG. 7) of an oxygen gas micro-sensor having an external magnet, as described herein.

FIGS. 10A and 10B are top plan views of an oxygen gas micro-sensor (left) that uses an external magnet, and a similar micro-sensor having an integrated thin film magnet (right).

DETAILED DESCRIPTION

Figure 1:
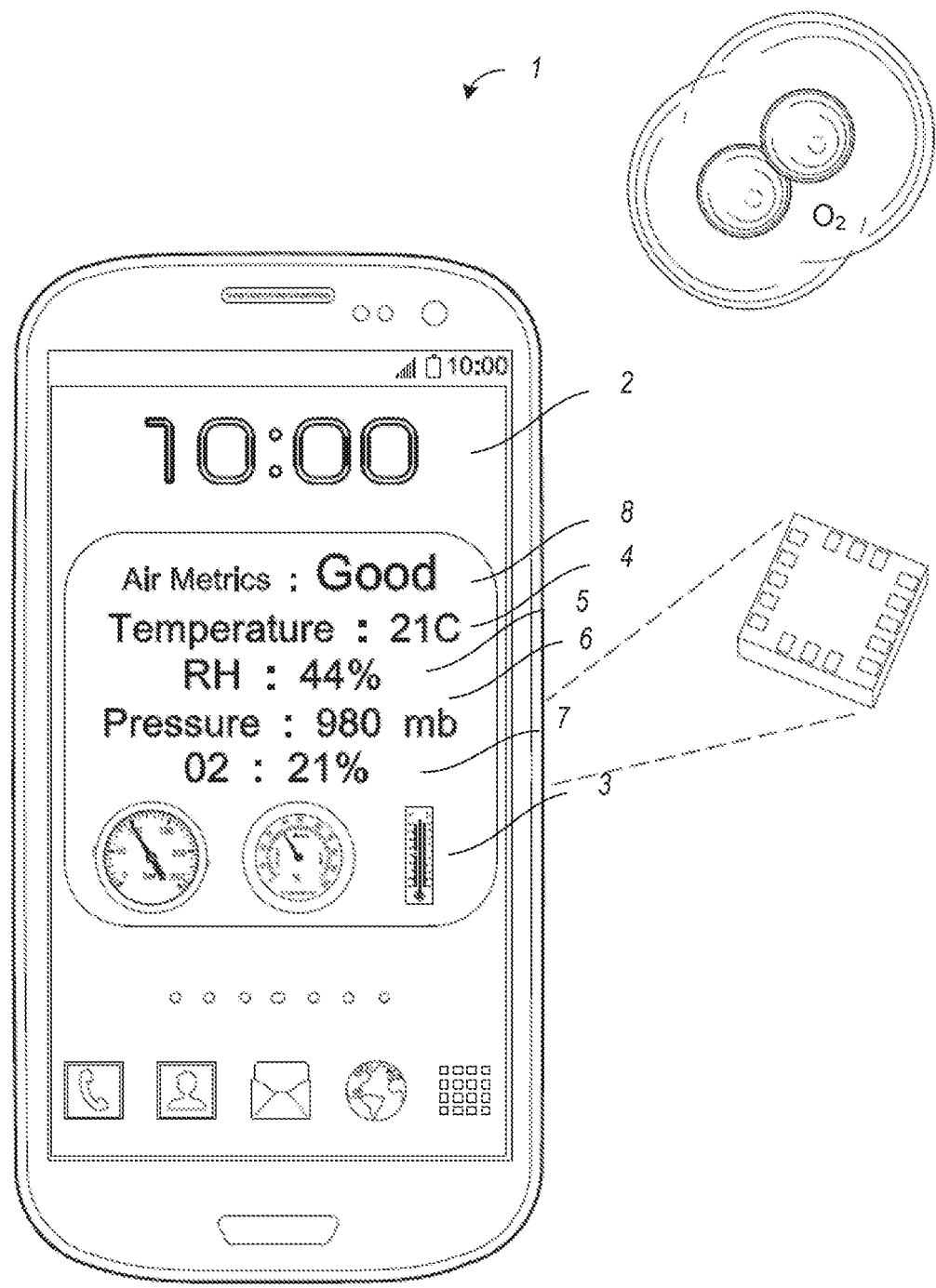
FIG. 1 is a screen shot of a smart phone running a weather station application that displays data from an on-board miniature oxygen gas micro-sensor.

It will be appreciated that, although specific embodiments of the present disclosure are described herein for purposes of illustration, various modifications may be made without departing from the spirit and scope of the present disclosure. Accordingly, the present disclosure is not limited except as by the appended claims.

In the following description, certain specific details are set forth in order to provide a thorough understanding of various aspects of the disclosed subject matter. However, the disclosed subject matter may be practiced without these specific details. In some instances, well-known structures and methods of semiconductor processing comprising embodiments of the subject matter disclosed herein have not been described in detail to avoid obscuring the descriptions of other aspects of the present disclosure.

Unless the context requires otherwise, throughout the specification and claims that follow, the word "comprise" and variations thereof, such as "comprises" and "comprising" are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

In the following description, certain specific details are set forth in order to provide a thorough understanding of various aspects of the disclosed subject matter. However, the disclosed subject matter may be practiced without these specific details. In some instances, well-known structures and methods of semiconductor processing comprising embodiments of the subject matter disclosed herein have not been described in detail to avoid obscuring the descriptions of other aspects of the present disclosure.

Unless the context requires otherwise, throughout the specification and claims that follow, the word "comprise" and variations thereof, such as "comprises" and "comprising" are to be construed in an open, inclusive sense, that is, as "including, but not limited to."

Reference throughout the specification to insulating materials or semiconducting materials can include various materials other than those used to illustrate specific embodiments of the transistor devices presented. The term "epitaxial silicon compounds" should not be construed narrowly to limit an epitaxially grown structure to Si or SiGe, for example, but rather, the term "epitaxial silicon compounds" is broadly construed to cover any compounds that can be grown epitaxially from a crystalline silicon surface.

Reference throughout the specification to conventional thin film deposition techniques for depositing silicon nitride, silicon dioxide, metals, or similar materials include such processes as chemical vapor deposition (CVD), low-pressure chemical vapor deposition (LPCVD), metal organic chemical vapor deposition (MOCVD), plasma-enhanced chemical vapor deposition (PECVD), plasma vapor deposition (PVD), atomic layer deposition (ALD), molecular beam epitaxy (MBE), electroplating, electro-less plating, and the like. Specific embodiments are described herein with reference to examples of such processes. However, the present disclosure and the reference to certain deposition techniques should not be limited to those described. For example, in some circumstances, a description that references CVD may alternatively be done using PVD, or a description that specifies electroplating may alternatively be accomplished using electro-less plating. Furthermore, reference to conventional techniques of thin film formation may include growing a film in situ. For example, in some embodiments, controlled growth of an oxide to a desired thickness can be achieved by exposing a silicon surface to oxygen gas or to moisture in a heated chamber.

Reference throughout the specification to conventional photolithography techniques, known in the art of semiconductor fabrication for patterning various thin films, includes a spin-expose-develop process sequence involving a photoresist. Such a photolithography sequence entails spinning on the photoresist, exposing areas of the photoresist to ultraviolet light through a patterned mask, and developing away exposed (or alternatively, unexposed) areas of the photoresist, thereby transferring a positive or negative mask pattern to the photoresist. The photoresist mask can then be used to etch the mask pattern into one or more underlying films. Typically, a photoresist mask is effective if the subsequent etch is relatively shallow, because photoresist is likely to be consumed during the etch process. Otherwise, the photoresist can be used to pattern a hard mask, which in turn, can be used to pattern a thicker underlying film.

Reference throughout the specification to conventional etching techniques known in the art of semiconductor fabrication for selective removal of polysilicon, silicon nitride, silicon dioxide, metals, photoresist, polyimide, or similar materials includes such processes as wet chemical etching, reactive ion (plasma) etching (RIE), washing, wet cleaning, pre-cleaning, spray cleaning, chemical-mechanical planarization (CMP) and the like. Specific embodiments are described herein with reference to examples of such processes. However, the present disclosure and the reference to certain deposition techniques should not be limited to those described. In some instances, two such techniques may be interchangeable. For example, stripping photoresist may entail immersing a sample in a wet chemical bath or, alternatively, spraying wet chemicals directly onto the sample.

Specific embodiments are described herein with reference to examples of integrated micro-sensors that have been produced; however, the present disclosure and the reference to certain materials, dimensions, and the details and ordering of processing steps are exemplary and should not be limited to those shown.

In the figures, identical reference numbers identify similar features or elements. The sizes and relative positions of the features in the figures are not necessarily drawn to scale.

FIG. 1 shows a smart phone 1 equipped with a miniature magnetic field-based gas sensor configured as an oxygen detector that can be used to monitor ambient air quality in real time. The miniature gas sensor, as described below, is designed to have a fast response time, on the order of milliseconds, about a thousand times faster than conventional gas concentration sensors. Furthermore, because the miniature gas sensor relies on a Hall effect sensing element, it consumes very little electrical power, making it feasible for deployment on a mobile computing device. Because the miniature gas sensor contains no reacting material, it has an essentially indefinite lifetime.

A shell of the smart phone 1 can be modified so as to allow exposure of the capacitive sensors to ambient air. An exemplary smart phone application ("app") can, for example, be programmed to display on the smart phone screen 2 weather station icons 3. The smart phone app can report measurements of temperature, relative humidity, pressure, and gas concentration (e.g., concentration of oxygen molecules $O_2$) via the readouts 4, 5, 6, and 7, respectively. The smart phone app can further provide an assessment of air quality 8 based on a comparison of the measurements to a selected standard. The standard can be pre-programmed or set by a user of the smart phone, for example.

Figure 2:
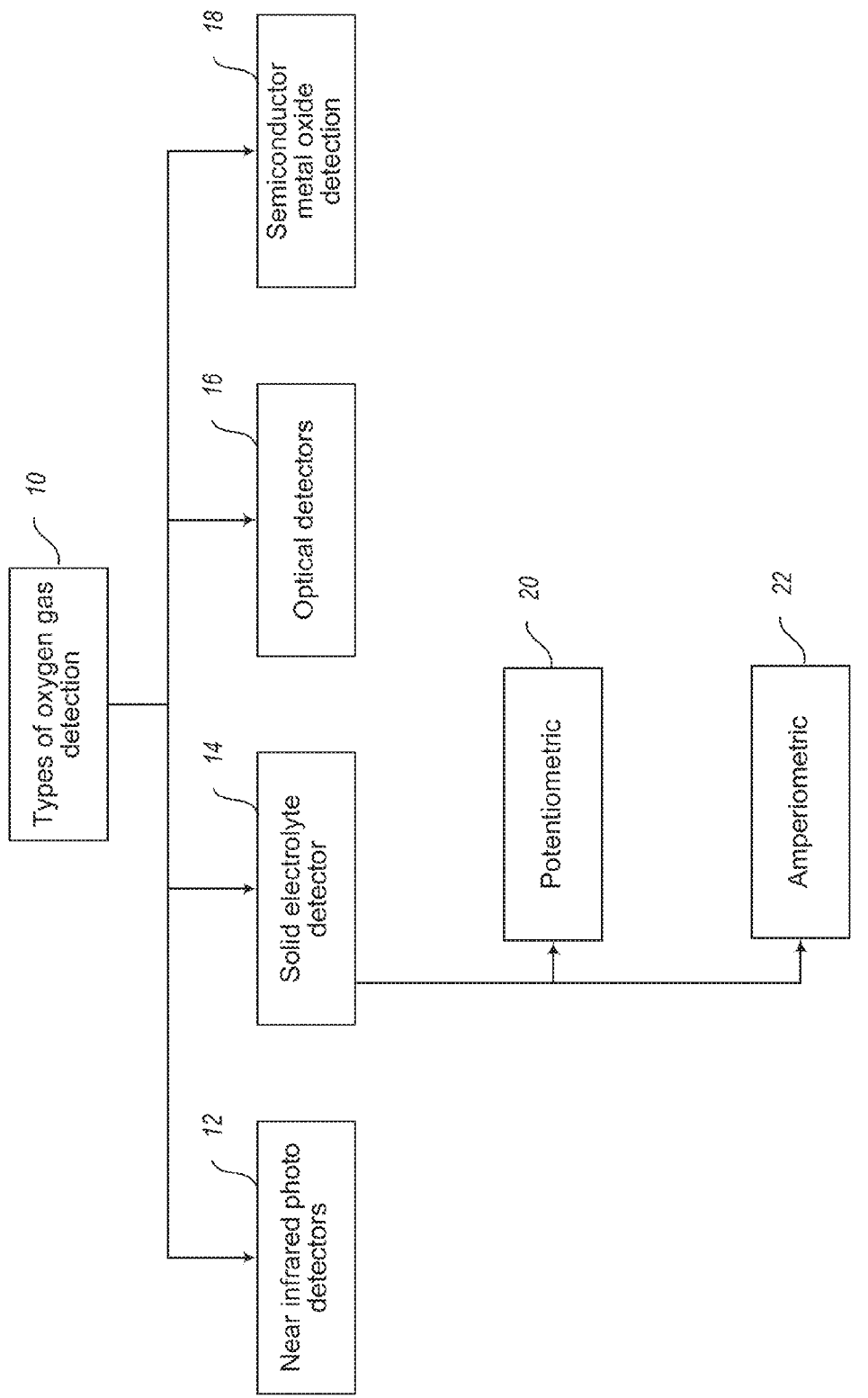
FIG. 2 is a tree diagram showing different types of existing oxygen gas detection devices.

Examples of different types of conventional oxygen gas detectors 10 are shown in FIG. 2. These include near infrared (NIR) photodetectors 12, solid electrolyte detectors 14, optical detectors 16, and semiconductor metal oxide detectors 18.

The NIR photodetector 12 can be used to measure gas absorption upon passing a NIR laser through oxygen gas.

The solid electrolyte detector 14 detects oxygen gas produced during an electrolytic chemical reaction, which can be a spontaneous, or potentiometric reaction 20, or a non-spontaneous, amperiometric reaction 22. In a potentiometric reaction 20, a spontaneous current can be produced by a reaction inside an electrolyte such as $Bi_2O_3$ or $Gd_2O_2$ doped with $CeO_2$ or YSZ. In an amperiometric reaction 22, an external source of current can drive oxygen from one electrode to another through the electrolyte.

Optical detectors 16 operate on the principle that oxygen quenches luminescence of an organic indicator such as fluoranthane or platinum-octaethylporphyrin dye.

Semiconductor metal oxide detectors 18 work on the principle that oxidation of a metal oxide semiconductor produces a change in resistance of the semiconducting material.

Figure 3:
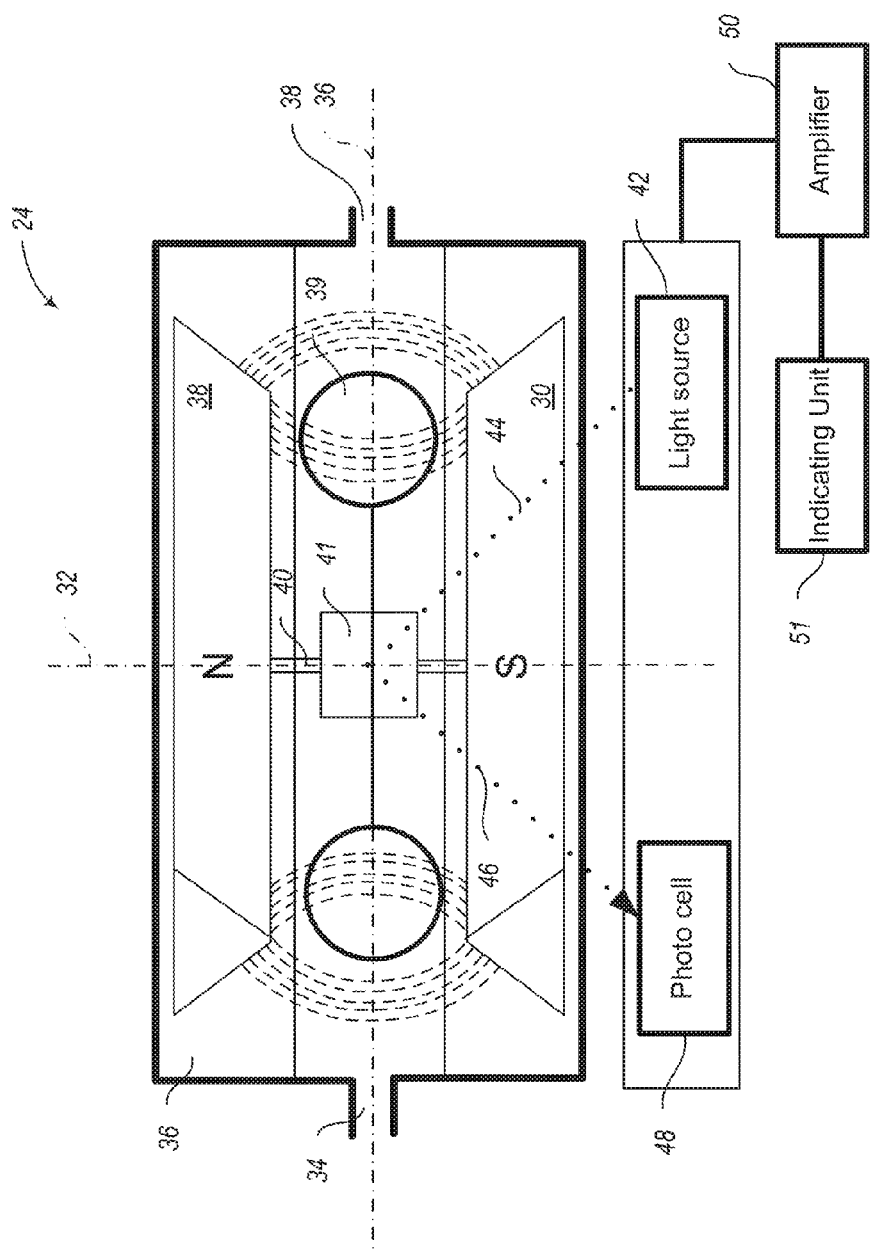
FIG. 3 is a schematic diagram of a conventional macroscale mechanical gas detection system.

Another type of oxygen gas sensor is a magnetic field-based oxygen sensor 24 such as the one shown in FIG. 3. The magnetic field-based oxygen sensor 24 relies on the paramagnetic property of oxygen gas. Because oxygen is paramagnetic, it can be influenced by magnetic fields. Furthermore, the presence of oxygen within a medium changes the magnetic susceptibility of the medium.

A conventional, macroscopic, magnetic field-based oxygen sensor 24 includes a measuring cell 26 in the form of a gas chamber housing a magnet. The magnet has a north pole 28 and a south pole 30 to establish a magnetic field oriented downward along a vertical axis 32. Oxygen gas enters the measuring cell 26 at a gas inlet 34, flows along a gas flow axis 36 and exits at a gas outlet 38. A dumbbell 39 aligned with the gas flow axis 36 can freely rotate about a spindle 40 in response to the flow of oxygen gas as the gas passes through the measuring cell 26. A plane mirror 41 can be positioned in the center of the dumbbell 39 between the poles of the magnet such that when the dumbbell 39 is deflected by gas flow, the mirror 41 tilts accordingly. External to the measuring cell 26, a light source 42 generates a source light beam 44 for incidence on the mirror 41. A conventional source light beam 44 may be, for example, a laser having power in the range of about 1-10 Watts. A reflected light beam 46 can then be detected at a photodetector 48. Signals from both the light source 42 and the photodetector 48 can be enhanced by an amplifier 50 to produce a measurement readout on an indicating unit 51. As long as the flow of oxygen gas through the measuring cell 26 remains constant, the reflected light beam 46 sensed by the photodetector 48 will also tend to have a constant intensity and be received at the same angle. However, when a change in the magnetic field strength causes the oxygen flow to vary, the angle of the mirror 41 will deflect in response to the change in gas flow. A deflection in the mirror angle will then cause fluctuation in the reflected light beam 46 sensed at the photodetector 48.

Figure 4A:
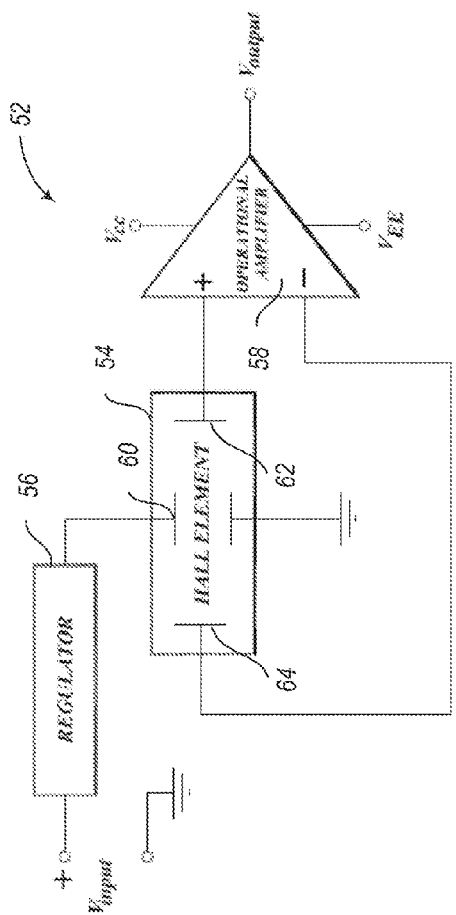
FIG. 4A is a schematic diagram of a prior art electrical circuit for use in implementing a Hall effect sensor.

FIG. 4A shows a schematic diagram of a Hall circuit 52 for use with a generic Hall effect sensor. The Hall effect describes a tendency for charges in a current-carrying wire to drift to one side of the wire when the wire is placed in an external magnetic field. This drift is due to the Lorentz force, $F=qv\times B$. As positive charges drift in one direction and negative charges drift in the opposite direction, a potential difference is set up across the wire, orthogonal to the direction of current flow. Such a potential difference is well known to those of skill in the art as a Hall potential, or Hall voltage. Hall effect sensors are often used to determine the sign of charge carriers in semiconductor devices, for example, in which both hole currents and electron currents can exist. In the present context, $O_2$ gas molecules, having a net dipole moment, can behave like free charges in motion, which causes the molecules to drift in a magnetic field, thus producing a Hall voltage.

The Hall circuit 52 includes a Hall effect sensor 54, a voltage regulator 56, and an operational amplifier (op-amp) 58. A bias voltage $V_{input}$ can be applied through the voltage regulator 56 at a bias voltage contact 60. The bias voltage can induce a Hall voltage between the terminals 62 and 64 of the Hall effect sensor 54. If the Hall voltage is then input to the op-amp 58, the Hall voltage can be amplified for ease of monitoring at $V_{output}$.

Figure 4B:
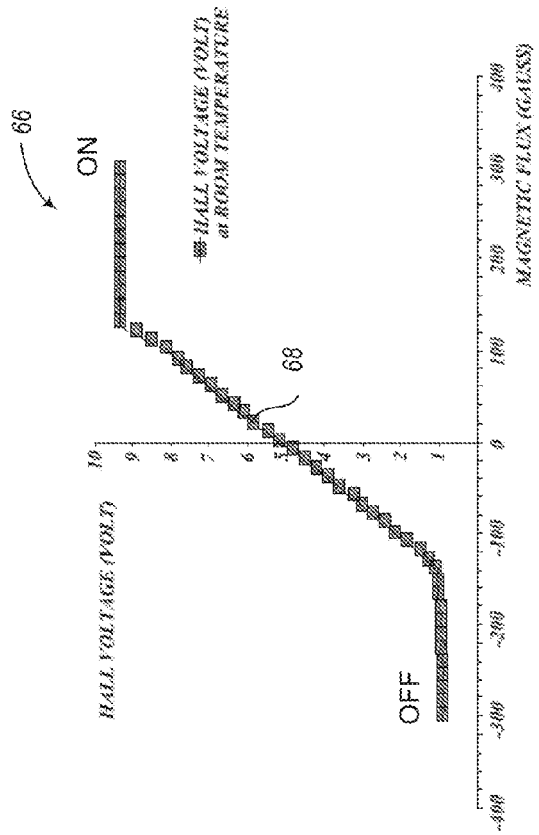
FIG. 4B is a plot of Hall voltage measured in response to an applied magnetic field for the Hall effect sensor shown in FIG. 4A.

FIG. 4B shows a switching plot 66 of voltage vs. applied magnetic field for the Hall effect sensor 54 used in a magnetic switch application. As the polarity of the applied magnetic field switches through the range of about −150 Gauss to +150 Gauss, a Hall voltage rises linearly from about 0 V (off state) to about 10 V (on state). Because the Hall voltage arises due to the paramagnetic response of the $O_2$ gas, the $O_2$ concentration affects the slope 68 of the switching plot 66. As the $O_2$ concentration increases, the slope 68 increases accordingly. At about 150 Gauss, the Hall voltage saturates and the slope 68 returns to zero.

Figure 5:
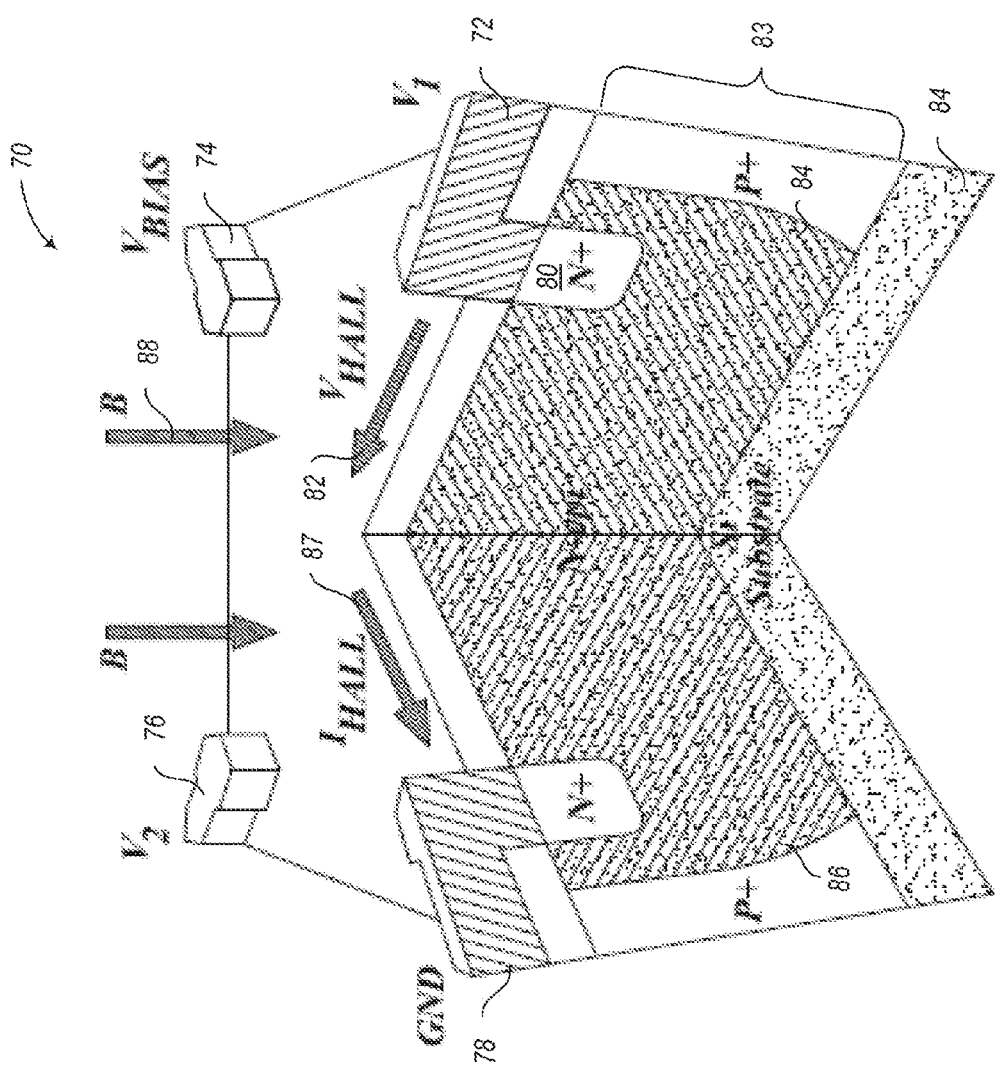
FIG. 5 is a cross section of a prior art integrated circuit implementation of a Hall effect sensor that may be used in the electrical circuit shown in FIG. 4A.

FIG. 5 shows a conventional semiconductor implementation of a Hall effect sensor 54 according to one exemplary embodiment. The Hall effect sensor 70 as shown is a four-terminal device having voltage contacts $V_1$ (72), $V_{bias}$ (74), and $V_2$ (76), and a ground contact (78). Such voltage contacts are typically made of a metal (e.g., Al). The $V_1$ voltage contact 72 and the ground contact 78 are coupled to an N+-doped region 80 within an epitaxially-grown surface layer 83 in contact with a crystalline silicon substrate 84. Within the surface layer 83 are formed P-N junctions 84 and 86. A downward-directed magnetic field B (88) can be applied externally as shown. Upon biasing the Hall effect sensor 70 by applying a bias voltage between the $V_{bias}$ voltage contact (74) and the ground contact (78), a current $I_{hall}$ (87) flows and a voltage $V_{hall}$ (82) can be measured between the voltage contacts $V_1$ (72) and $V_2$ (76).

FIGS. 6A-6C show a time sequence of snapshots of a miniature magnetic field-based gas sensor 98, according to one embodiment used to carry out a method of detecting a paramagnetic gas. Such a miniature magnetic field-based gas sensor 98 that is appropriate for consumer electronics desirably operates at power levels in the range of about 1-10 mW. This power range represents about a 1000× power reduction compared to the large scale system described above with reference to FIG. 3. In addition, it is advantageous for the lifetime of such a miniature magnetic field-based gas sensor 98 to exceed that of a conventional sensor, which typically operates for about 1-5 years. The lifetime of the miniature magnetic field-based gas sensor 98 is, in theory, unlimited, because it includes no moving parts and does not consume material in chemical reactions. Thus, the miniature magnetic field-based sensor 98 is more durable than other types of gas sensors.

The miniature magnetic field-based gas sensor 98 includes a gas sensing cavity 100 positioned in an external downward-directed magnetic field 88. As shown in FIG. 6A, the gas sensing cavity 100 is empty, prior to introducing a gas sample. In one embodiment, the gas sensing cavity 100 can have the shape of a rhombus having a width of about 50 microns and a height of about 10 microns. The external downward-directed magnetic field 88 can be supplied by an external permanent magnet having a magnetic north pole 104 and a magnetic south pole 106. The orientation of the external downward-directed magnetic field 88 is indicated by vertical magnetic field lines. The gas sensing cavity 100 can be formed within a glass carrier 108, for example, by an oxide etching process, such as a wet etch using a pure, concentrated hydrofluoric acid that etches glass at a rate of about 15 μm/minute at 50 C. The glass carrier 108 can then be inverted and bonded to the crystalline silicon substrate 84 in which an integrated Hall effect sensor 70 has been formed. The crystalline silicon substrate 84 can have a thickness of, for example, within the range of about 50 microns-150 microns. The glass carrier 108 can have a thickness within the range of about 700 microns-1 mm. The Hall effect sensor 70 is designed to make a four-point Hall measurement, e.g., two currents and two voltages. In particular, the Hall effect sensor 70 provides leads to measure the current at the second pad 115 and a voltage difference between the first pad sensor contact 114 and the second sensor contact pad 115. The voltage contacts $V_1$ (72) and $V_2$ (76) in FIG. 5 are similar to the sensor contact pads 114 and 115, respectively. A volt meter 116 can be used to monitor potential differences ΔV (Hall voltage 82) between the first sensor contact pad 114 and the second sensor contact pad 115. Prior to introducing a sample, the volt meter 116 may read, for example, 1 mV.

The method of detecting oxygen gas using the magnetic field-based gas sensor 98 entails applying a magnetic field to the miniature magnetic field-based gas sensor 98 (FIG. 6A), introducing a gas sample (FIG. 6B), and measuring a Hall voltage indicative of a presence of oxygen in the gas sample (FIG. 6C). As shown in FIG. 6B, when a gas sample containing oxygen molecules 118 (e.g., air) is introduced into the gas sensing cavity 100, initially the volt meter 116 still measures 1 mV. This is because the oxygen molecules are still randomly distributed within the sensing cavity 100. Then, because it has the property of paramagnetism, the oxygen gas responds to the applied magnetic field 88 as shown by the segregation 122 of $O_2$ molecules in the gas sensing cavity 100. Some of the $O_2$ molecules move toward the magnetic north pole 104, while others move toward the magnetic south pole 106, according to the effect of the magnetic field 88 on the dipole moments of the oxygen atoms. As the oxygen gas becomes magnetized, the susceptibility decreases the magnetic field intensity within the gas sensing cavity 100. Segregation 122 of the $O_2$ molecules in the magnetic field 88 thus results in a decrease in the electric potential difference across the integrated Hall effect sensor 70 as detected by the volt meter 116. After a short time interval, the volt meter 116 reads 0.8 mV, indicating development of a Hall voltage 82 of 0.2 V across the gas sample, which can be related to an oxygen concentration within the gas sample (FIG. 6C).

The integrated Hall effect sensor 70 used in the present context is highly sensitive, being capable of detecting a momentary magnetic field of a few μTesla. Therefore, it can feature a very fast response time (e.g., milliseconds or microseconds), as compared with a macroscopic conventional oxygen detector (e.g., the one shown in FIG. 3) which is typically capable of sensing magnetic fields of 30-50 mTesla, and has a typical response time of 10 seconds-1 minute.

Figure 7:
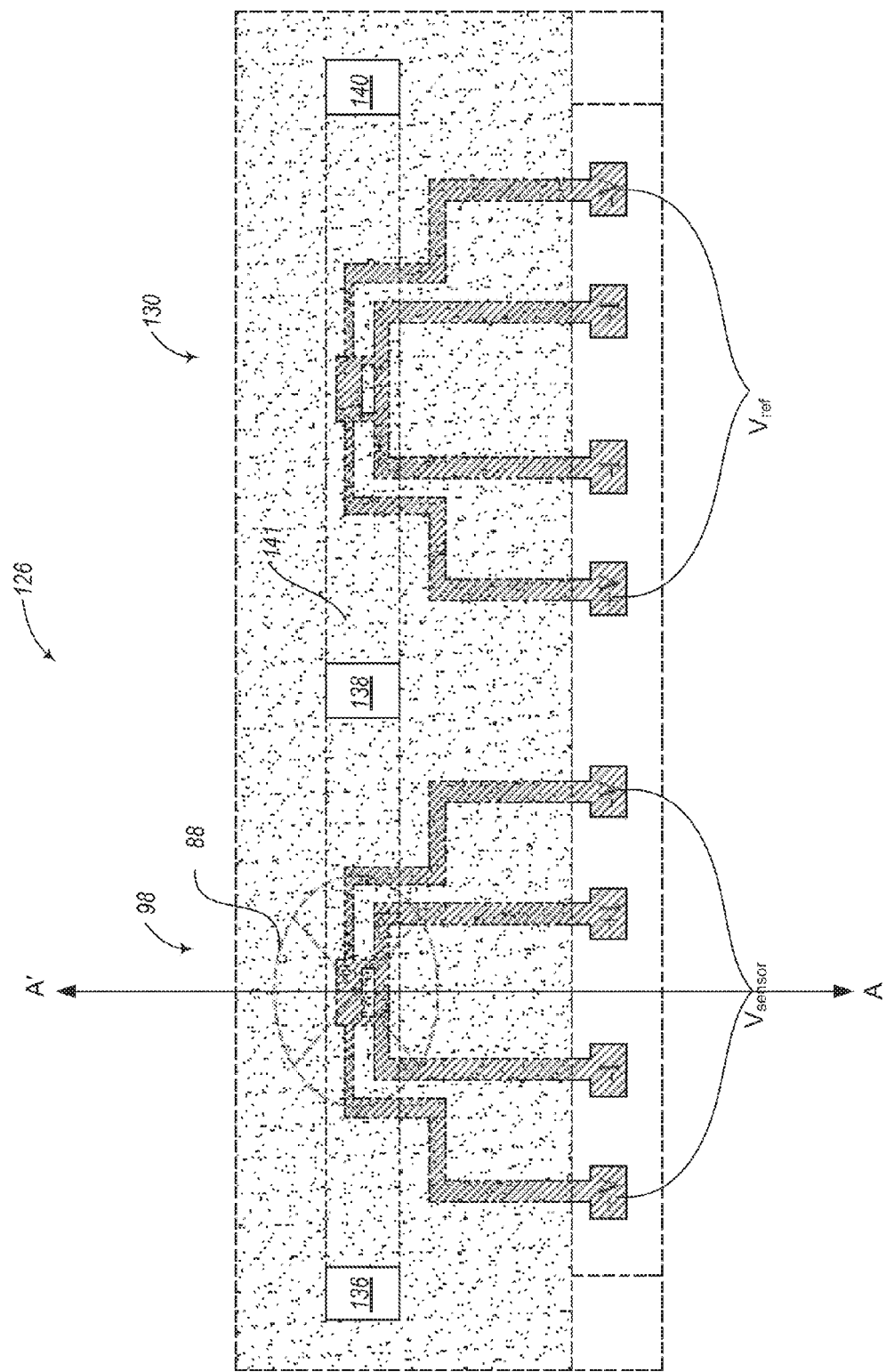
FIG. 7 is a top plan view of a differential oxygen gas micro-sensor (left) and a reference sensor (right) as described herein.

The miniature magnetic field-based gas sensor 98 may be configured to operate alongside a control sensor. For example, FIG. 7 shows a differential micro-structure 126 that senses oxygen gas ($O_2$) by measuring a differential Hall effect. The differential micro-structure 126 includes the miniature magnetic field-based gas sensor 98 and a reference element 130 that share a common micro-channel 141. The views of the miniature magnetic field-based gas sensor 98 shown in FIGS. 6A-6C are cross-sectional views taken along cut line A-A' of the present view shown in FIG. 7. The miniature magnetic field-based gas sensor 98 allows monitoring of $O_2$ gas in a sample of ambient air that enters the micro-channel 141 of the differential micro-structure 126 through one or more openings 136, 138, and 140. The openings 136, 138, and 140 are sized and dimensioned to allow a constant volume of a few microliters of air to be maintained within the micro-channel 141 which spans both of the sensing elements. The openings 136, 138, and 140 can be made, for example, by drilling. Thus, the reference element 130 is in fluid communication with the gas sensing cavity 100 (i.e., the reference element contains the same gas as the gas sensing cavity 100). A magnetic field 88 is then applied to the miniature magnetic field-based gas sensor 98, in a direction orthogonal to the plane in which the sensors lie, as indicated by the "X." Meanwhile, no magnetic field is applied to the reference element 130. In response to the applied magnetic field 88, $O_2$ molecules in the miniature magnetic field-based gas sensor 98 tend to segregate, giving rise to a lateral charge separation, whereas $O_2$ segregation does not occur in the reference element 130. The charge separation causes an electric potential difference to form between the two poles V+ and V−. This potential difference is then measured as the voltage $V_{sensor}$, for comparison with a reference voltage $V_{reference}$. The voltage difference $$\Delta V_{out} = V_{sensor} - V_{reference} \quad (1)$$

represents a change in magnetization of the oxygen gas in response to the applied magnetic field. In general, magnetization M varies with the applied magnetic field 88 according to the relationship $$M = xB, \quad (2)$$

in which x is proportional to the volume susceptibility of the $O_2$ gas, the susceptibility being a material constant. The voltage difference $\Delta V_{out}$ 144 is thus a differential Hall voltage.

Figure 8:
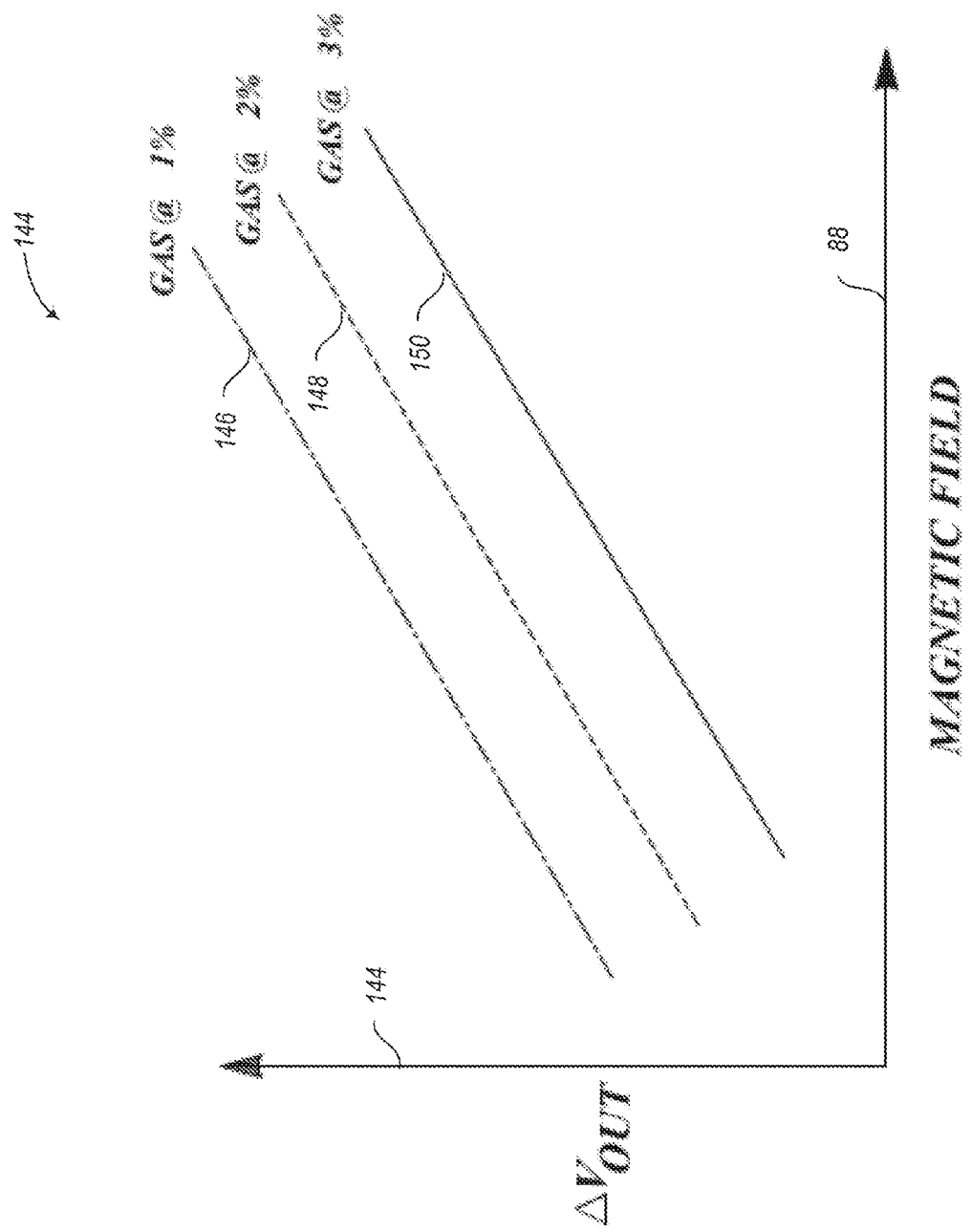
FIG. 8 is a plot of differential output voltage as a function of magnetic field strength for three different gas concentrations, as measured by a gas micro-sensor that uses the Hall effect.

FIG. 8 shows a family of curves 144 of measured values of the differential Hall voltage $\Delta V_{out}$ (144) as a function of the external, downward-directed magnetic field strength B (88) for three gas samples, each containing a different concentration of $O_2$. As expected from equation (2), each of the curves 144 is linear. A gas sample containing 1% oxygen produces a linear curve 146; a gas sample containing 2% oxygen produces a linear curve 148, and a sample containing 3% oxygen produces a linear curve 150. As the gas concentration increases, the external, downward-directed magnetic field 88 is less effective in segregating the $O_2$ molecules, so the differential voltage is lower for the same applied magnetic field strength.

Figure 9B:
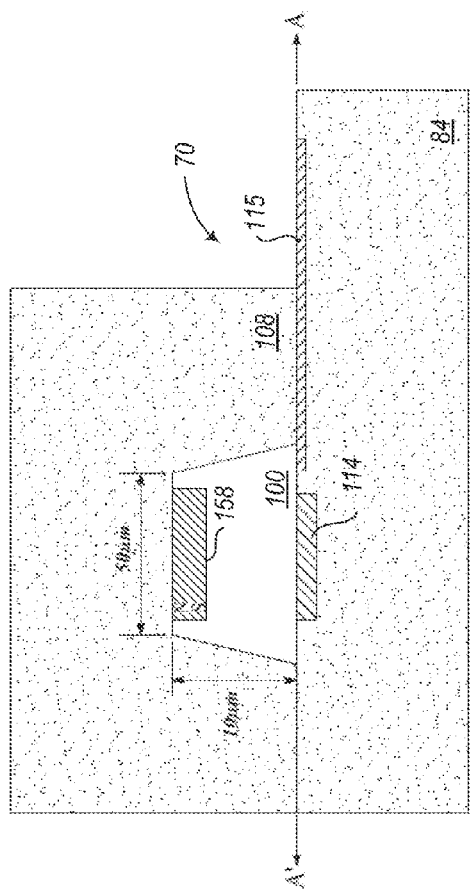
FIG. 9B is a cross-sectional view of a micro-sensor in which an integrated magnetic thin film is used to magnetize a gas sensing cavity.
Figure 9A:
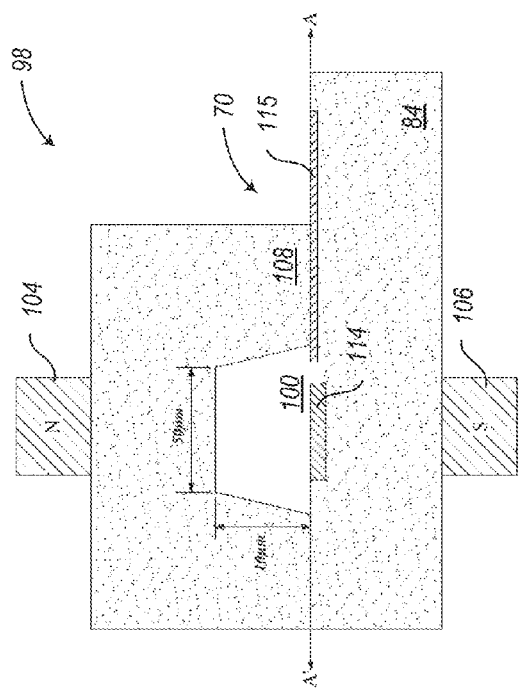
FIG. 9A is a reproduction of the cross section shown in FIG. 6A, in which an external magnet is used to magnetize a gas sensing cavity.

The side view of the miniature magnetic field-based gas sensor 98 is reproduced in FIG. 9A, for comparison with a corresponding side view of an alternative oxygen sensor 156 shown in FIG. 9B. The alternative oxygen sensor 156 features an integrated thin film permanent magnet 158 in place of the external permanent magnetic poles 104, 106. The integrated thin film permanent magnet 158 may be, for example, an Iron-Cobalt-Nickel (FeCoNi) magnet having a thickness of about 1 micron. Such an integrated thin film permanent magnet 158 can be deposited and patterned after etching the gas sensing cavity 100 from the glass carrier 108. After the glass carrier 108 is placed over the crystalline silicon substrate 84, the integrated thin film permanent magnet 158 extends downward toward the center of the gas sensing cavity 100.

The top plan view of the miniature magnetic field-based gas sensor 98 shown in FIG. 7 is reproduced in FIG. 10A, for comparison with a corresponding top plan view of the alternative oxygen sensor 156 shown in FIG. 10B. The alternative oxygen sensor 156 also includes the microchannel 141 including the gas inlet opening 136 and the gas outlet opening 138. The sensors 98 and 156 function according to the same principles and share substantially the same structure, except for the geometry of the magnets. Thus, the alternative oxygen sensor 156 is a substitute for the miniature magnetic field-based gas sensor 98, with the exception that the alternative oxygen sensor 156 includes the thin film permanent magnet 158. It is noted that the thin film permanent magnet 158 has a smaller size than the external magnet characterized by magnetic poles 104, 106. Whereas the external downward-directed magnetic field 88 is represented by a large circumscribed "X" in FIG. 10A, the corresponding thin film magnetic field 162 produced by the thin film permanent magnet 158 shown in FIG. 10B is represented by a small rectangle. However, the size of the magnet itself does not necessarily dictate the strength of the magnetic field produced thereby. Field lines associated with the external downward-directed magnetic field 88 extend farther out along the micro-channel 141, whereas field lines produced by the thin film permanent magnet 158 may tend to be more concentrated in the region of the gas sensing cavity 100, directly above the sensor contact pads 114 and 115.

Figure 11A:
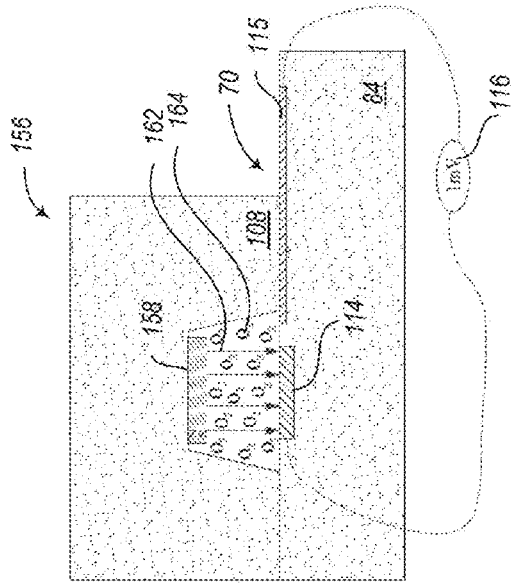
FIGS. 11A-11C are cross-sectional views of an oxygen gas micro-sensor that includes an integrated magnetic thin film, as described herein.
Figure 11B:
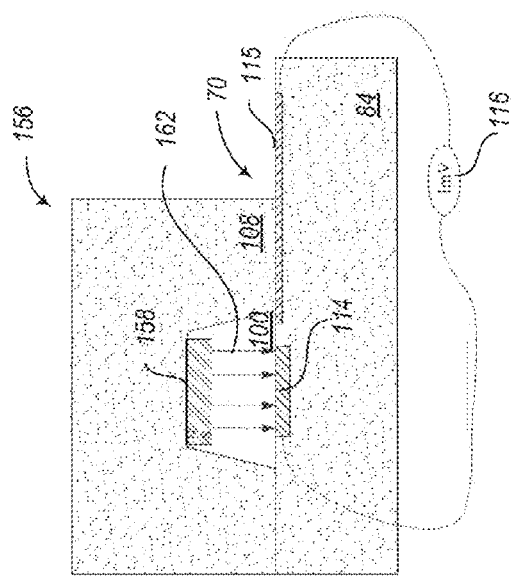
Figure 11C:
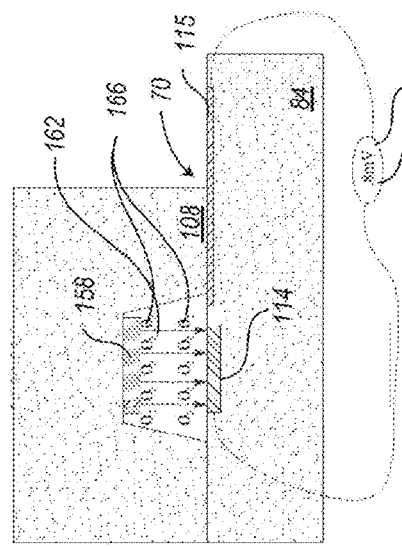

FIGS. 11A-11C show a time sequence of snapshots of the alternative oxygen sensor 156. The alternative oxygen sensor 156 operates at power levels similar to those used for the miniature magnetic field-based gas sensor 98. Also, the lifetime of the alternative oxygen sensor 156 is comparable to the extended lifetime of the miniature magnetic field-based gas sensor 98. The alternative oxygen sensor 156 includes the gas sensing cavity 100 positioned in the thin film magnetic field 162 produced by the thin film permanent magnet 158. As shown in FIG. 11A, the gas sensing cavity 100 is empty prior to introducing a gas sample. The orientation of the thin film magnetic field 162 is indicated by vertical magnetic field lines. As described above with reference to FIGS. 6A-6C, the volt meter 116 can be used to monitor potential differences $\Delta V$ (Hall voltage 82) between the first sensor contact pad 114 and the second sensor contact pad 115. Prior to introducing a sample, the volt meter 116 may read, for example, 1 mV.

As shown in FIG. 11B, when a gas sample containing oxygen molecules 164 (e.g., air) is introduced into the gas sensing cavity 100, initially the volt meter 116 still measures 1 mV. This is because the oxygen molecules are still distributed randomly within the gas sensing cavity 100. Then, because it has the property of paramagnetism, the oxygen gas responds to the applied thin film magnetic field 162 as shown by the segregation 166 of $O_2$ molecules in the gas sensing cavity 100 (FIG. 11C). Some of the $O_2$ molecules move toward the magnetic north pole, while others move toward the magnetic south pole, according to the Hall effect. The segregation 166 of the $O_2$ molecules in the thin film magnetic field 162 again tends to decrease the magnetic field strength, and in turn, the electric potential difference, across the integrated Hall effect sensor 70 as detected by the volt meter 116. After a short time interval the volt meter 116 reads 0.8 mV, indicating development of a Hall voltage 82 of 0.2 V across the gas sample which can be related to an oxygen concentration within the gas sample (FIG. 11C). Like that in the miniature magnetic field-based gas sensor 98, the integrated Hall effect sensor 70 in the alternative oxygen sensor 156 is capable of detecting a momentary magnetic field in the range of a few μTesla. Therefore, the alternative oxygen sensor 156 can also feature a very fast response time (e.g., milliseconds or microseconds), as compared with a macroscopic conventional oxygen detector (e.g., that shown in FIG. 3).

In one embodiment, some or all of the logic circuits that form the op-amp 58 and other logic devices of the sensing circuits are formed in the same substrate 84 that contains the contact pads 114 and 115. This reduces the distance that a signal needs to travel from the analog sense location 100 to the electrical detection and measurement circuit, which includes the op-amp 58 and other circuits. It also reduces the amount of noise that can enter the signal prior to being placed in digital form. In such embodiments, the substrate 84 is a monocrystalline substrate in which transistors and logic circuits can be formed. In other embodiments, the substrate 84 is a polycrystalline or amorphous substrate. Thus, in one embodiment, the substrate 84 can be polycrystalline silicon, amorphous silicon, quartz, sapphire, or other substrate material.

Figure 12:
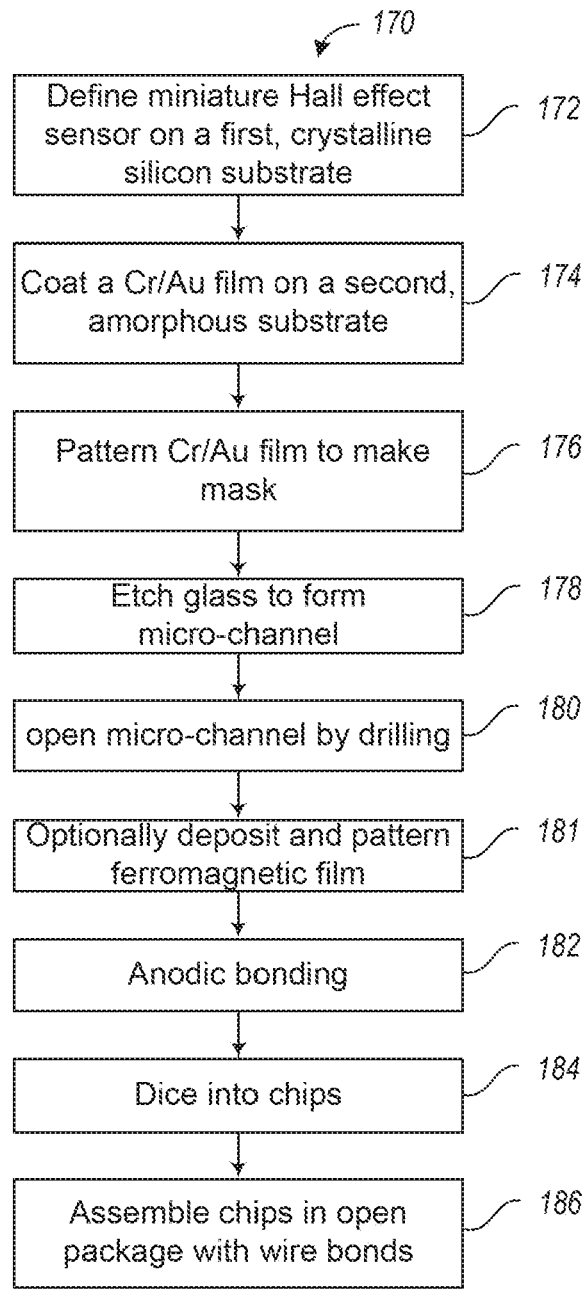
FIG. 12 is a flow diagram showing a sequence of processing steps in a method of fabricating a gas micro-sensor as described herein.

FIG. 12 shows an exemplary sequence of steps in a fabrication process 170 for making a miniature magnetic field-based oxygen sensor.

At 172 a miniature Hall effect sensor (e.g., a sensor resembling the conventional semiconductor-based Hall effect sensor 70) can be defined on the crystalline silicon substrate 84 according to the cross section shown in FIG. 5.

At 174, the top metal layer of the Hall effect sensor 70 can be patterned to provide electrical sensor contact pads 114 and 115 ($V_1$ and $V_2$ contacts, respectively), at which a Hall voltage can be measured.

At 176, a metal film (e.g., a chromium-gold (Cr—Au) film) can be deposited onto the amorphous (e.g., glass) substrate 108 and patterned to form a micro-channel mask. The chromium-gold film may be in the form of a bi-layer wherein the chromium thickness is about 250 nm and the gold thickness is about 5000 nm.

At 178, the amorphous substrate 108 can be etched through the micro-channel mask to form the micro-channel 141 so as to have a channel depth of about 20 μm.

Once the micro-channel 141 is formed, at 180, the openings 136, 138, and 140 can be drilled into the amorphous substrate 108 to provide access for ambient air to enter and be maintained at a constant volume in the micro-channel 141. A flow of air is not needed to perform the Hall effect measurements. The area of the openings 136, 138, 140 can be about $(100 \ \mu m)^2$.

Optionally, at 181, a ferromagnetic film (e.g., an FeCoNi film) can be deposited and patterned on a surface of the micro-channel 141 to form the integrated thin film permanent magnet 158. The thin film permanent magnet 158 is sized and dimensioned to fit, or to define, the gas-sensing cavity 100 for the alternative oxygen sensor 156.

At 182, the amorphous substrate 108 can be bonded to the crystalline silicon substrate 84 using anodic bonding, metal eutectic bonding, or an adhesive bonding technique. Examples of adhesives that may be used in bonding such substrates include epoxy, or a polyimide film.

At 184, the bonded substrates 108 and 84 can be diced into individual sensor chips.

At 186, the sensor chips can be assembled into an open package. The open package may support one or more sensor chips that are stacked with, or placed adjacent to, other sensor chips and/or integrated circuit chips carrying signal processing circuitry, microprocessors, electronic memory, and the like. During a packaging process, the chips may be electrically coupled to one another by wire bonding.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
    a silicon substrate;
    a glass substrate on the silicon substrate;
    a gas sensor, including:
        a first channel in the glass substrate;
        a first magnet positioned on the glass substrate and adjacent to the first channel, the first magnet having a magnetic field; and
        a first Hall effect sensor positioned on the silicon substrate and adjacent to the first channel; and
    a reference element, including:
        a second channel in the glass substrate, the second channel being in fluidic communication with the first channel; and
        a second Hall effect sensor positioned on the silicon substrate and adjacent to the second channel.

2. The device of claim 1 wherein the first magnet is positioned in the first channel and spaced from the silicon substrate.

3. The device of claim 1 wherein the gas sensor includes a second magnet positioned on the silicon substrate, the first magnet being spaced from the second magnet by the silicon substrate and the glass substrate.

4. The device of claim 3 wherein the first magnet is a first magnetic pole, and the second magnet is second magnetic pole.

5. The device of claim 1 wherein the first channel and the second channel are formed between the silicon substrate and the glass substrate.

6. The device of claim 5 wherein the glass substrate includes a plurality of openings that extend through the glass substrate, and the first channel and the second channel are in fluidic communication with an external environment through the plurality of openings.

7. The device of claim 1 wherein the gas sensor includes a first plurality of contact pads electrically coupled to the first Hall effect sensor, portions of the first plurality of contact pads are positioned outside of the first channel, the reference element includes a second plurality of contact pads electrically coupled to the second Hall effect sensor, portions of the second plurality of contact pads are positioned outside of the second channel.

8. A device, comprising:
    a silicon substrate;
    a glass substrate on the silicon substrate;
    a channel in the glass substrate;
    a first Hall effect sensor in the silicon substrate;
    an integrated fixed magnet positioned on the glass substrate, in the channel, and adjacent to the first Hall effect sensor; and
    a second Hall effect sensor in the silicon substrate, the channel extending from the first Hall effect sensor to the second Hall effect sensor.

9. The device of claim 8 wherein the glass substrate includes a plurality of openings, and the channel is in fluidic communication with an environment external to the channel through the plurality of openings.

10. The device of claim 8, further comprising:
    a plurality of contact pads electrically coupled to the first Hall effect sensor and the second Hall effect sensor, portions of the plurality of contact pads being positioned outside of the channel.

11. The device of claim 8 wherein the magnet is configured to apply a magnetic field in the channel.

12. A device, comprising:
    a silicon substrate;
    a glass substrate on the silicon substrate;
    a channel in the glass substrate, the channel having a first side and a second side opposite to the first side;
    a first Hall effect sensor in the silicon substrate and adjacent to the first side of the channel;
    first and second magnets having a magnetic field through the first side of the channel, the first magnet being spaced from the second magnet by the silicon substrate and the glass substrate; and
    a second Hall effect sensor in the silicon substrate and adjacent to the second side of the channel.

13. The device of claim 12 wherein the glass substrate includes a plurality of openings, the channel being in fluidic communication with an environment external to the channel through the plurality of openings.

14. The device of claim 12, further comprising:
    a first plurality of contact pads electrically coupled to the first Hall effect sensor, portions of the first plurality of contact pads being positioned outside of the channel; and
    a second plurality of contact pads electrically coupled to the second Hall effect sensor, portions of the second plurality of contact pads being positioned outside of the channel.

15. The device of claim 12 wherein the first magnet is a first magnetic pole, and the second magnet is a second magnetic pole.

16. The device of claim 1 wherein a portion of the first Hall effect sensor is aligned with the first channel and the first magnet.

\* \* \* \* \*